United States Patent
Kido et al.

(10) Patent No.: US 6,544,242 B1
(45) Date of Patent: *Apr. 8, 2003

(54) DISPOSABLE BODY FLUIDS ABSORBENT ARTICLE

(75) Inventors: Tsutomu Kido, Ehime-ken (JP); Hiroyuki Soga, Kagawa-ken (JP); Toshio Inoue, Kagawa-ken (JP); Koji Kawamura, Kagawa-ken (JP)

(73) Assignee: Uni-Charm Corporation, Ehime-ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 820 days.

(21) Appl. No.: 08/882,787

(22) Filed: Jun. 26, 1997

(30) Foreign Application Priority Data

Jun. 28, 1996 (JP) .............................. 8-170410

(51) Int. Cl.[7] .......................... A61F 13/15; A61F 13/20
(52) U.S. Cl. .................. 604/385.13; 604/389
(58) Field of Search ............... 604/385.1, 386, 604/387, 389–391, 385.2, 396, 393, 385.13

(56) References Cited

U.S. PATENT DOCUMENTS

| | | | | | |
|---|---|---|---|---|---|
| 3,800,796 | A | * | 4/1974 | Jacob | 604/390 |
| 4,643,729 | A | * | 2/1987 | Laplanche | 604/390 |
| 4,787,897 | A | * | 11/1988 | Torimae et al. | 604/389 |
| 4,963,140 | A | * | 10/1990 | Robertson | 604/389 |
| 5,071,414 | A | | 12/1991 | Elliott | |
| 5,575,784 | A | * | 11/1996 | Ames-Ooten et al. | 604/389 |
| 5,591,521 | A | * | 1/1997 | Arakawa et al. | 604/389 |
| 5,626,573 | A | * | 5/1997 | Igaue et al. | 604/389 |
| 5,735,835 | A | * | 4/1998 | Kawaguchi et al. | 604/385.2 |
| 5,807,371 | A | * | 9/1998 | Toyada | 604/387 |

FOREIGN PATENT DOCUMENTS

| | | | | |
|---|---|---|---|---|
| EP | 0 321 234 | | 6/1989 | |
| EP | 0324578 | * | 7/1989 | 604/390 |
| EP | 0 570 980 | | 5/1993 | |
| EP | 0623330 | * | 11/1994 | 604/389 |
| JP | 58-22908 | | 12/1983 | |
| JP | 6-77722 | | 1/1994 | |

* cited by examiner

Primary Examiner—Dennis Ruhl
Assistant Examiner—K. M. Reichle
(74) Attorney, Agent, or Firm—Lowe Hauptman Gilman & Berner, LLP

(57) ABSTRACT

A disposable body fluids absorbent article is provided on an outer surface of a backsheet thereof with a tape fastener for fastening the used article in a rolled up condition for disposal. The tape fastener includes a fixed end portion secured to the outer surface of the backsheet, a free end portion longitudinally opposite the fixed end portion, an elastically stretchable portion extending longitudinally between these opposite end portions, and an adhesive portion extending longitudinally between the free end portion and the elastically stretchable portion and releasably bonded to the outer surface of the backsheet.

6 Claims, 2 Drawing Sheets

DISPOSABLE BODY FLUIDS ABSORBENT ARTICLE

BACKGROUND OF THE INVENTION

This invention relates generally to disposable body fluids absorbent articles such as disposable diapers, training pants and sanitary napkins and, more particularly, to such articles provided with means by which the used article is fastened in a rolled up condition thereof for disposal.

It is well known to provide disposable body fluids absorbent articles with a tape fastener adapted to fasten the used article in a rolled up condition for hygienic disposal thereof.

For example, Japanese Laid-Open Utility Model Application No. Sho58-22908 discloses a disposable diaper in which one end portion of an adhesive tape is fixed to the diaper backsheet and the free end portion extends outward beyond the diaper waist-line edge. After use, the diaper soiled with excretions may be rolled up with the backsheet outside toward the free end portion of the tape and then the diaper thus rolled up may be fastened by the free end portion.

In addition, Japanese Laid-Open Utility Model Application No. Hei6-77722 discloses a pull-on disposable diaper in which a tape fastener extending vertically of the diaper is fixed at its one end to an outer surface of the backsheet. This tape fastener is normally folded longitudinally thereof and may be unfolded in its actual use to extend outward beyond the waist-line edge of the waist-opening. In this manner, the soiled diaper may be fastened by the unfolded tape fastener in a rolled up condition thereof for disposal as with the diaper disclosed in the Japanese Laid-Open Utility Model Application No. Sho58-22908.

In the diaper disclosed in the Japanese Laid-Open Utility Model Application No. Sho58-22908, a long adhesive tape will result in a longer free end portion that extends outward beyond the waist line edge, interfering with comfortable wear of the diaper. Accordingly, it is difficult in practice to employ a relatively long adhesive tape.

In the case of the diaper disclosed in the Japanese Laid-Open Utility Model Application No. Hei6-77722, a longer adhesive tape will result in a more bulky tape when in a folded condition. Consequently, this folded adhesive tape may catch the baby's eye and the baby may play with the tape. Once the adhesive tape has been unfolded by the baby, it is not easy to refold and, in consequence, a troublesome labor is forced upon the mother.

The problem common to both of the well known diapers mentioned is that, after the soiled diaper has been removed from the baby, rolled up and tightly fastened by the adhesive tape stretched with a high tension, the adhesive once anchored to the rolled diaper may often peel off from the outer surface of the rolled diaper under the tension of the adhesive tape unless the anchoring of the adhesive tape is reliably firm.

SUMMARY OF THE INVENTION

In view of the above problem, it is a principal object of the invention to provide a disposable body fluids absorbent article, such as a disposable diaper, with a relatively short tape fastener that allows the article to be easily held in its rolled up condition without the tape fastener peeling from the outer surface of the rolled article once the tape fastener has been anchored to the outer surface.

The object set forth above is achieved, according to the invention, with a disposable body fluids absorbent article comprising a topsheet on a skin-contactable side, a backsheet on a skin non-contactable side, and a tape fastener adapted to fasten the body fluids absorbent article soiled with excretions in a rolled up condition thereof in a predetermined direction.

The tape fastener comprises a fixed end portion secured to an outer surface of the backsheet and a free end portion longitudinally opposite to the fixed end portion which is adapted to be held by the user's fingers. An elastically stretchable portion extends between the fixed and free end portions. An adhesive portion extends longitudinally between the free end portion and the elastically stretchable portion with an inner surface of the adhesive portion facing the outer surface of the backsheet releasable bonded to the outer surface.

In another aspect of the invention, the elastically stretchable portion comprises an elastically stretchable sheet having an elongation percentage in the longitudinal direction of 100–1500% and an elastic recovery percentage of 10–90% relative to the elongation percentage.

In another aspect of the invention, the fixed end portion, the free end portion and the adhesive portion are formed by sheet material substantially less stretchable than the elastically stretchable portion.

In yet another aspect of the invention, after the adhesive portion releasably bonded to the outer surface of the backsheet has been peeled off from the outer surface of the backsheet, the tape fastener can be longitudinally stretched until a portion of the tape fastener, at least including the free end portion and the adhesive portion, stretches past an outer edge of the rolled up body fluids absorbent article to reach a position lying outward beyond the outer edge.

The invention allows the tape fastener used to fasten the disposable body fluids absorbent article to be shortened sufficiently to avoid any concern that the tape fastener might prevent the article from being smoothly worn, since the tape fastener has appropriate stretchability. In addition, the tape fastener is not readily peeled off from the article which has been fastened in a rolled up condition thereof by the stretched tape fastener, since the contractile force of this tape fastener is progressively reduced as time elapses after the tape fastener has been stretched to fasten the rolled up article.

Other and further objects, features and advantages of the invention will appear more fully from the following description.

DESCRIPTION OF THE PREFERRED EMBODIMENT

Figure 1:
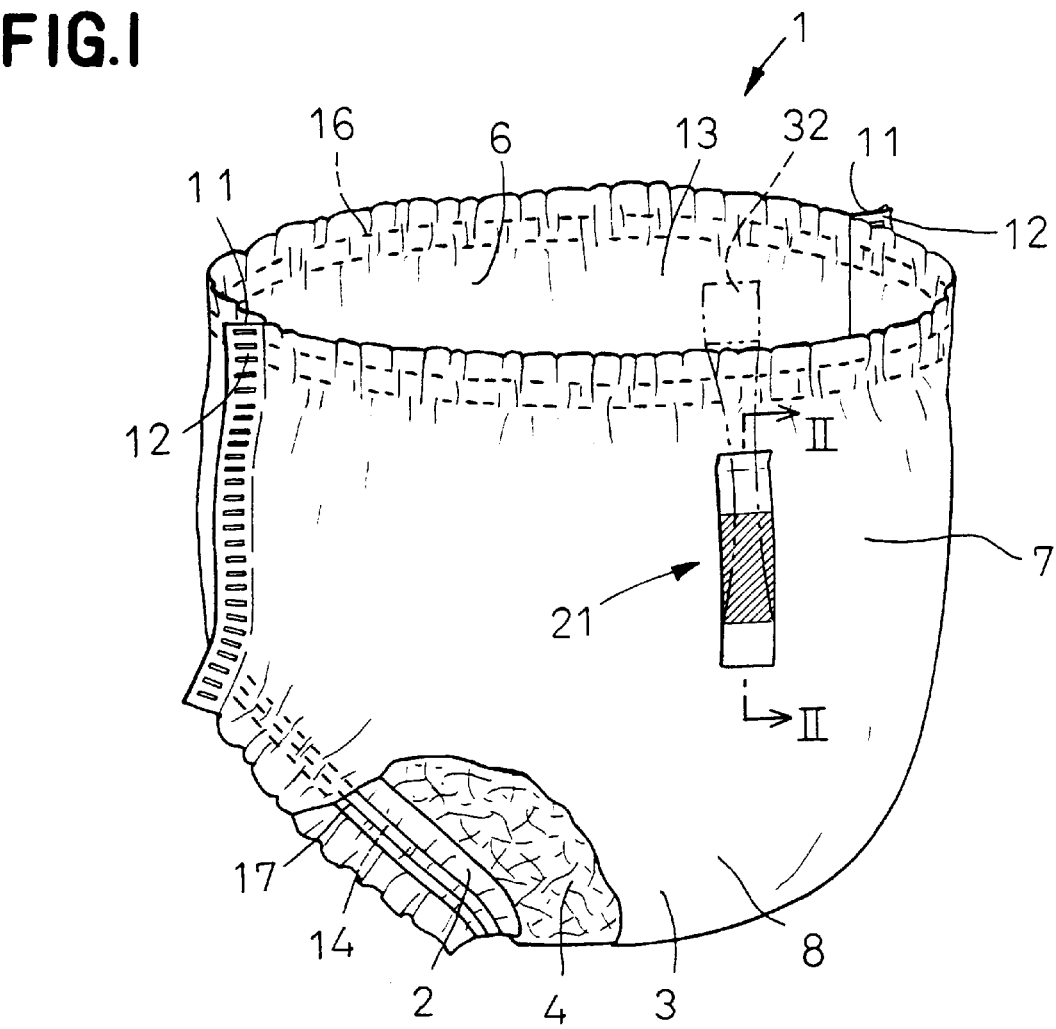
FIG. 1 is a perspective view showing a pull-on disposable diaper type as an embodiment of the invention as partially broken away.

A pull-on disposable diaper 1 shown by FIG. 1 in a perspective view as partially broken away is a specific embodiment of the inventive body fluids absorbent article. The diaper 1 comprises a liquid permeable topsheet 2 on a skin-contactable side, a liquid-impermeable backsheet 3 on a skin non-contactable side and a liquid-absorbent core 4 extending between these two sheets 2, 3. The diaper 1 has a front waist region 6, a rear region 7 and a crotch region 8 extending between these two regions 6, 7. The front and rear waist regions 6, 7 are joined together along transversely opposite side edges 11, 12 thereof to define a waist-opening 13 and a pair of leg-openings 14. The waist-opening 13 as well as the leg-openings 14 are provided along peripheral edges thereof with elastic members 16 and 17, respectively, each comprising a plurality of elastic elements. The elastic member 16 serves to fit the diaper 1 around the waist of the wearer and the elastic members 17 serve to fit the diaper 1 around the legs of the wearer. The elastic members 16, 17 are secured in elastically stretched conditions thereof to an inner surface of at least one of the topsheet 2 and backsheet 3 at portions of these sheets 2, 3 extending outward beyond a peripheral edge of the absorbent core 4. The rear waist region 7 is provided at a circumferentially middle. position with a tape fastener 21 oriented vertically on the diaper 1.

Figure 2:
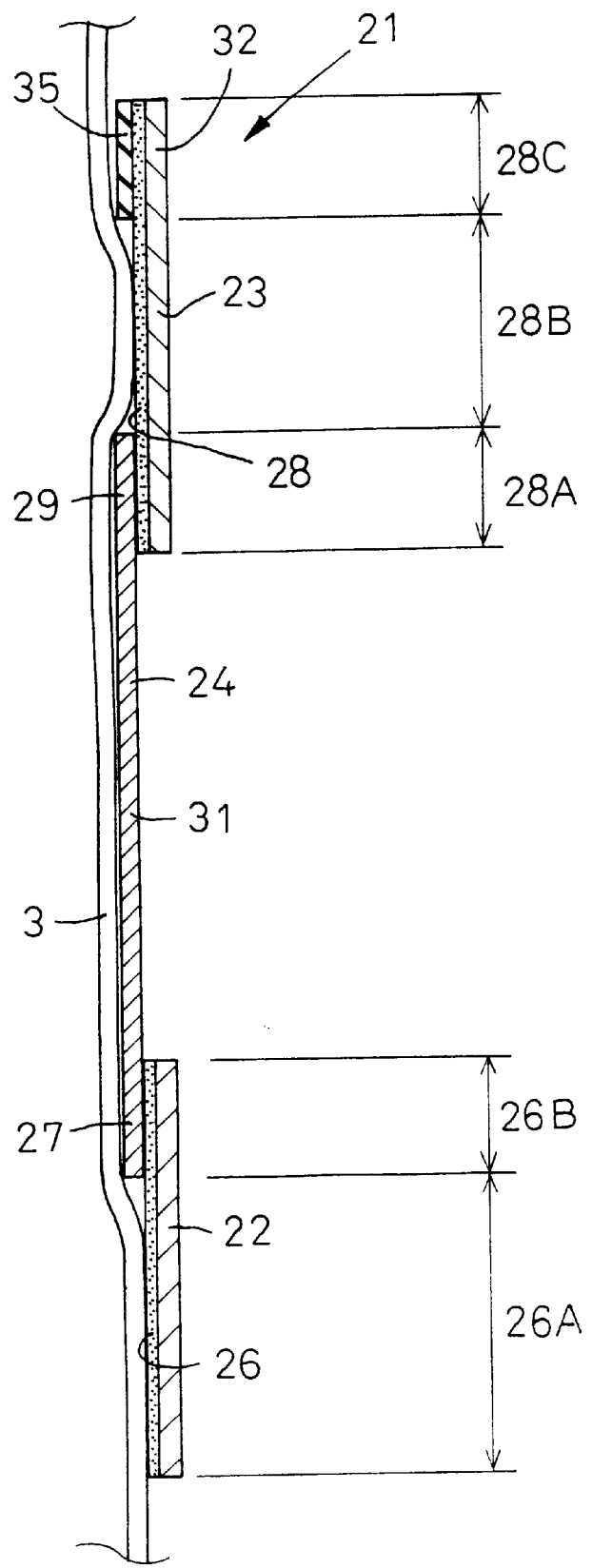
FIG. 2 is a sectional view taken along line II—II in FIG. 1, showing an important part of the diaper.

FIG. 2 is a sectional view taken along line II—II in FIG. 1, showing a construction of the tape fastener 21. The tape fastener 21 comprises, as viewed in the longitudinal direction (i.e., vertical direction), a lower end member 22, an upper end member 23 and an intermediate member 24 extending between the lower and upper end members 22, 23. The lower end member 22 has its entire inner surface applied with a first adhesive 26 so that the lower end member 22 is bonded to a lower end portion 27 of the intermediate member 24 over a second applied zone 26B of the first adhesive 26 and to an outer surface of the backsheet 3 over a first adhesive zone 26A of the first adhesive 26. Similarly, the upper end member 23 has its inner surface applied with second adhesive 28 so that the upper end member 23 is bonded to an upper end portion 29 of the intermediate member 24 over a third adhesive zone 28A of the second adhesive 28, to the outer surface of the backsheet 3 over a fourth adhesive zone 28B of the second adhesive 28 and to a film member 35 to be held by the user's fingers over a fifth adhesive zone 28C of the second adhesive 28. All these adhesive zones except the fourth adhesive zone 28B (i.e., the first, second, third and fifth adhesive zones 26A, 26B, 28A, 28C) bond the members 22, 23, 24, 35 to opposed portions of the backsheet 3, respectively, so firmly that these members and the backsheet practically cannot be separated from one another. Over the fourth adhesive zone 28B, on the other hand, the tape fastener 21 is releasably bonded to the backsheet 3. The condition of releasable bonding may be achieve by applying to the outer surface of the backsheet 3 a mold release agent and/or regulating an adhesive power of the second adhesive 28.

The intermediate member 24 has an elastically stretchable portion 31 of a predetermined length between the lower end member 22 and the upper end member 23. Since the upper portion 32 of upper end member 23 has its inner surface bonded to the film member 35, the upper end portion 32 may be held by the user's fingers to separate the tape fastener 21 from the backsheet 3 within the fourth adhesive zone 28B.

The lower end member 22 and the end member 23 forming parts of the tape fastener 21 may be made of sheet-like material such as substantially non-stretchable plastic film or nonwoven fabric. An example of such a sheet-like material is polyester film having a thickness of 0.02–0.3 mm. The intermediate member 24 may be made of elastically stretchable sheet-like material, preferably, stretchable sheet-like material having an elongation percentage of 100–1500% and a percentage of elastic recovery after such elongation of 10–90%. An example of such a sheet-like material is elastomer film having a thickness of 0.02–0.3 mm. It should be understood that the percentage of elastic recovery is based on a length measured after a strip of 10 mm×50 mm cut from the sheet in question is stretched until a desired elongation percentage is reached within 5 seconds and held in this state for one minute, then the stretching force is released and left in this released state for an additional one minute.

Figure 3:
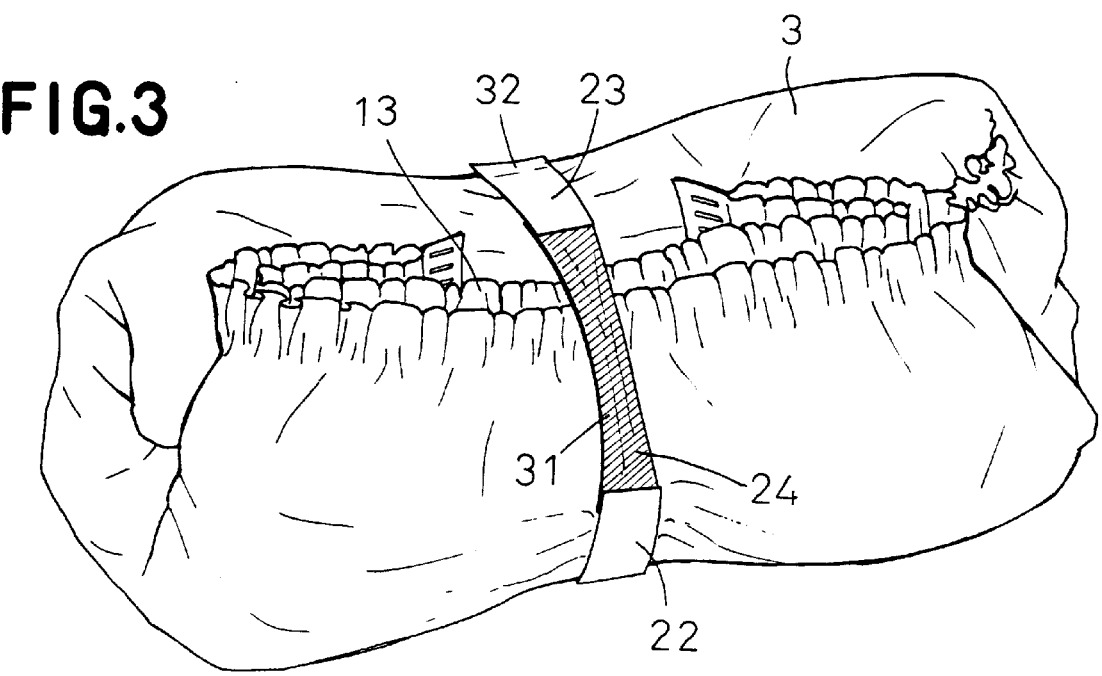
FIG. 3 is a perspective view showing the diaper as rolled up.

FIG. 3 is a perspective view showing the diaper 1 rolled up and fastened by the tape fastener 21. The diaper 1 may be rolled up from the crotch region 8 toward the waist-opening 13 as shown, or from the front waist region 6 toward the rear waist region 7 with the topsheet 2 inside after transversely opposite side edges of the diaper 1 have been cut apart back and forth along their bonded lines. Thereafter the tape fastener 21 may be pulled up with the upper end portion 32 held by the user's fingers (as indicated by imaginary lines in FIG. 1) so as to peel the fourth adhesive zone 28B off from the backsheet 3 and thereby stretch the stretchable portion 31 of the intermediate member 24 until the upper end of the stretchable portion 31 stretches beyond the waist opening, whereupon the tape fastener 21 may be anchored on the outer surface of the backsheet 3. After the diaper 1 has been left in this rolled up condition for a time, a stretch stress initially generated in the stretchable portion 31 is relieved and a contractile force in the stretchable portion 31 tending to peel the fourth adhesive zone 28B off the backsheet 3 is correspondingly relieved. Consequently the fourth adhesive zone 28B with the lapse of time reduces any apprehension that the fourth adhesive zone 28B might be peeled off from the backsheet 3 under the contractile force of the stretchable portion 31.

While it is also possible without departing from the scope of the invention to apply the one and same strip of elastically stretchable tape successively in its longitudinal direction with adhesive agents having different natures and thereby to obtain a desired tape fastener 21, instead of using the lower end member 22, the upper end member 23 and the intermediate member 24, the tape fastener 21 obtained in this matter will be inconvenient in that the elasticity of the basic tape may prevent the upper end portion 32 from being readily held by the user's fingers from being and in that it will be difficult, during the process of manufacturing the diaper 1, to bond the portion corresponding to the first adhesive zone 26A to the backsheet 3. Bonding of the lower end member 22 and the upper end member 23 to the backsheet 3 is facilitated when the members 22, 23 are non-stretchable and high in their rigidities. These members 22, 23 are preferably formed by the strips provided separately of the intermediate member 24.

The position at which the tape fastener 21 is provided on the diaper 1 is not limited to the position as shown with respect to the specific embodiment. A position at which the diaper 1 is provided, a full length of the tape fastener 21, a length of the stretchable portion 31, and upper and/lower limits of the length to which the stretchable portion 31 is stretched may be determined depending on a manner in which the used diaper 1 is to be rolled up. However, it is desired to dimension and construct the tape fastener 21 so that its free end can be stretched beyond the outer edge of the rolled up diaper 1.

The tape fastener 21 of this invention can be useful not only for the diaper 1 but also for the other body fluids absorbent articles such as training pants, pants for incontinent patients, sanitary napkins, bandages and the like.

Having described the invention as related to the embodiment shown in the accompanying drawings, it is our intention that the invention be not limited by any of the details of description, unless otherwise specified, but rather be construed broadly within its spirit and scope as set out in the accompanying claims.

What is claimed is:

1. A disposable body fluids absorbent article, comprising a topsheet having a skin-contactable side adapted to contact a wearer, a backsheet joined to the topsheet, an absorbent disposed between said topsheet and said backsheet, and a tape fastener extending in a longitudinal direction of the backsheet and adapted to fasten the body fluids absorbent article soiled with excretions in a rolled up condition thereof in a predetermined direction, wherein:

said tape fastener comprises a fixed end portion secured to an outer surface of said backsheet, a free end portion located longitudinally opposite to said fixed end portion and adapted to be held by a wearer's fingers, an elastically stretchable portion extending longitudinally between said fixed end portion and said free end portion and an adhesive portion extending longitudinally between said free end portion and said elastically stretchable portion with an inner surface of said adhesive portion facing the outer surface of said backsheet and releasably directly bonded to said outer surface.

2. The body fluids absorbent article according to claim 1 wherein, after said adhesive portion releasably bonded to the outer surface of said backsheet has been peeled off from the outer surface of said backsheet, said tape fastener can be longitudinally stretched until a portion of said tape fastener at least including said free end portion and said adhesive portion can get beyond an outer edge of said body fluids absorbent article rolled up and reach a position lying outward beyond said outer edge.

3. The article of claim 1, wherein each of said fixed, free and stretchable portions include a longitudinal axis, and said longitudinal axes of said fixed, free end and stretchable portions extend coaxial to each other when normally attached to the backsheet prior to use around a rolled article after soiling.

4. The article of claim 1, wherein said fixed end portion, said free end portion and said adhesive portion are formed by a sheet material having stretch characteristics rendering said sheet material less stretchable than said elastically stretchable portion.

5. The article of claim 1, wherein each of the fixed, free and stretchable portions include a longitudinal axis that reside in a plane which is perpendicular to the longitudinal axis of the article in its rolled up condition.

6. A method of disposal of a disposable body fluids absorbent article in which a tab fastener has a fixed end portion secured to an outer surface of a backsheet of the article, a free end portion located opposite to said fixed end portion and being releasably adhesively attached to the backsheet prior to use, and an elastically stretchable portion extending longitudinally between said fixed and free end portions, comprising the steps of:

(a) releasing the free end portion from direct releasable attachment to the backsheet;

(b) rolling up the absorbent article from a crotch region of said backsheet toward a waist opening or from a front waist region of said backsheet toward a rear waist region, by rolling said backsheet along the longitudinal axis of said article, the resulting rolled up article having a longitudinal axis in its rolled configuration that is perpendicular to the longitudinal axis of the article in its unrolled configuration; and (c) extending the tape fastener by stretching the elastically stretchable portion so that the free end portion is adhesively secured to another portion of the article located on an opposite side of the waist opening.

* * * * *